United States Patent [19]
Tanaka et al.

[11] Patent Number: 6,034,231
[45] Date of Patent: *Mar. 7, 2000

[54] HUMAN CNP GENE AND PRECURSOR PROTEIN

[75] Inventors: Shoji Tanaka, Hyogo-ken; Kayoko Fuchimura, Osaka; Yasunori Tawaragi, Saitama-ken; Hisayuki Matsuo, Osaka; Kenji Kanagawa, Miyazaki-ken; Naoto Minamino, Osaka, all of Japan

[73] Assignee: Suntory Limited, Osaka, Japan

[ * ] Notice: This patent is subject to a terminal disclaimer.

[21] Appl. No.: 07/765,830

[22] Filed: Sep. 26, 1991

[30] Foreign Application Priority Data

Sep. 27, 1990 [JP] Japan .................................. 2-259698

[51] Int. Cl.[7] .......................... C07H 17/00; C07K 14/00; C07K 14/575
[52] U.S. Cl. ..................... 536/23.51; 536/23.1; 530/325; 530/300
[58] Field of Search ............................... 536/27; 530/350, 530/325

[56] References Cited

FOREIGN PATENT DOCUMENTS

WO89/12069  12/1989  WIPO .

OTHER PUBLICATIONS

Biochemical and Biophysical Research Communications, vol.168, No.2, Apr. 30, 1990, pp. 863–870.
Biochemical and Biophysical Research Communications, vol.170, No. 2, 1990, pp. 973–979.
Biochemical and Biophysical Research Communications, vol.175, No. 2, Mar. 15, 1991, pp. 645–651.
Seilhamer et al. 1989 Biochem Biophys Res Commun 165:650–658.
Vbsuk et al 1986. Biochem–Biophys Res. Commun 136:396–403.
Minamino et al 1990 Biochem Biophys Res Commun 170:973–979.
Tawaragi et al 1991 Biochem Biophys Res Commun. 175:645–651.

*Primary Examiner*—Karen Cochrane Carlson
*Attorney, Agent, or Firm*—Cushman Darby & Cushman IP Group of Pillsbury Madison & Sutro LLP

[57] ABSTRACT

The gene of a human CNP (human C-type natriuretic peptide), as well as the hCNP precursor protein that is encoded by said gene. The hCNP precursor is represented by the following amino acid sequence.

Met His Leu Ser Gln Leu Leu Ala Cys Ala

Leu Leu Leu Thr Leu Leu Ser Leu Arg Pro

Ser Glu Ala Lys Pro Gly Ala Pro Pro Lys

Val Pro Arg Thr Pro Pro Ala Glu Glu Leu

Ala Glu Pro Gln Ala Ala Gly Gly Gly Gln

Lys Lys Gly Asp Lys Ala Pro Gly Gly Gly

Gly Ala Asn Leu Lys Gly Asp Arg Ser Arg

Leu Leu Arg Asp Leu Arg Val Asp Thr Lys

Ser Arg Ala Ala Trp Ala Arg Leu Leu Gln

Glu His Pro Asn Ala Arg Lys Tyr Lys Gly

Ala Asn Lys Lys Gly Leu Ser Lys Gly Cys

Phe Gly Leu Lys Leu Asp Arg Ile Gly Ser

Met Ser Gly Leu Gly Cys.

The hCNP precursor and its derivatives are novel and have natriuretic and hypotensive activities.

7 Claims, 6 Drawing Sheets

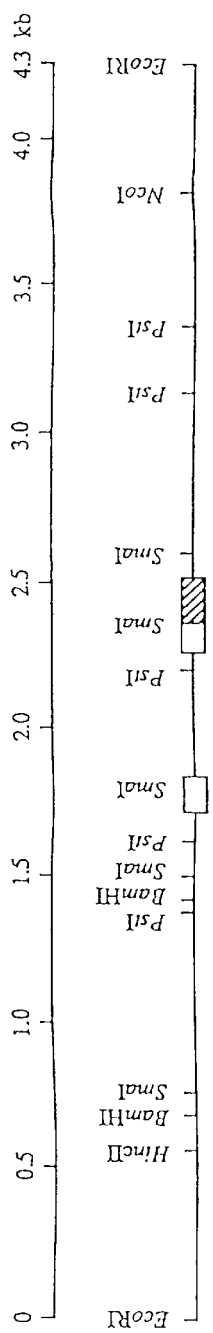
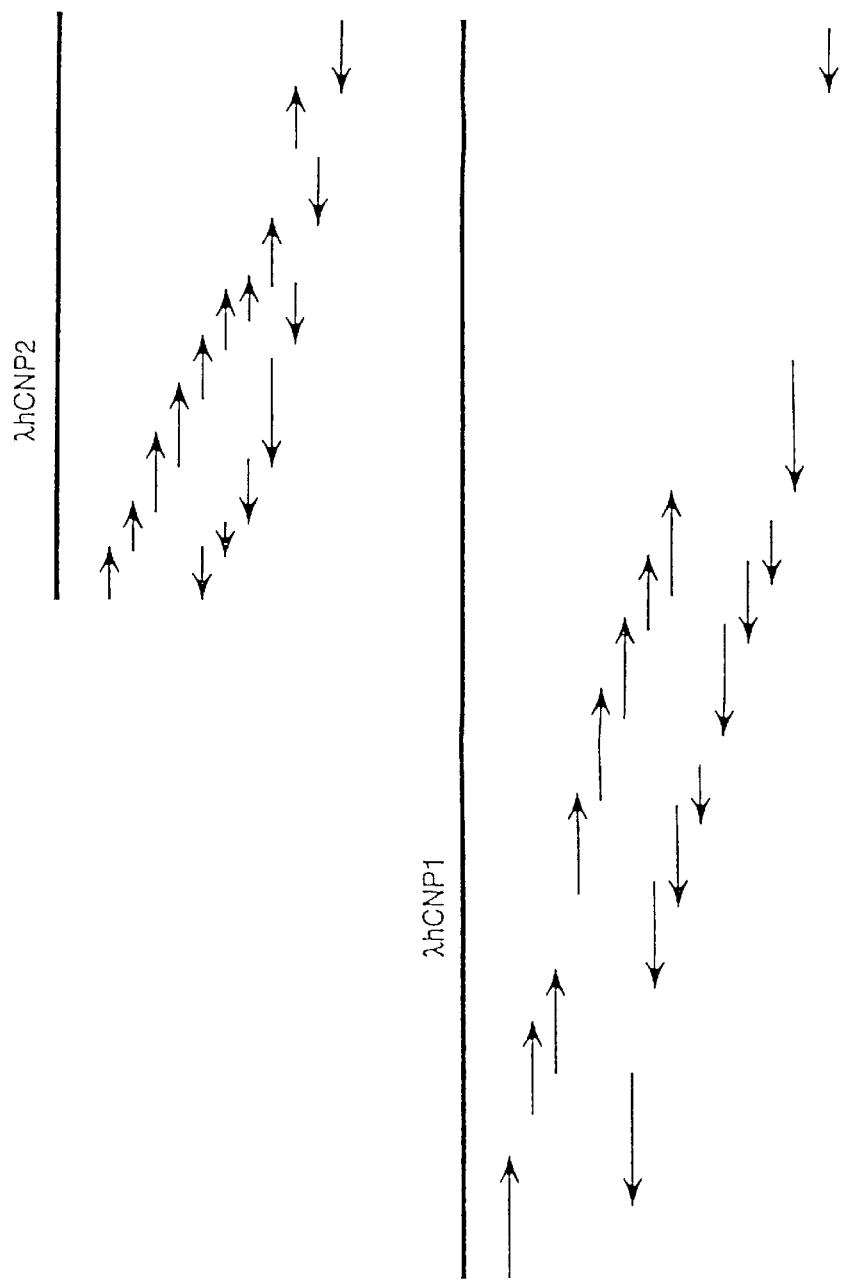
Fig. 1(a)
Fig. 1(b)

Fig. 2-1

```
GAATTCCTGTTTCCTAAGCAAAGTGACCTGTGTAGTGGTTGCTCC
AATGTTGTGAGTCAGGGTATGAGAGTGGGAAGGGGTAGCCTGAGA      90
AAGGTGCCGACAGAGCAGACCATGATGCGGCCGCCTTAGCAGCTC
TGGGACCAGGCTCACTACCACGGAGGGAAGAGGGAGGCTTGGAGG     180
GAACCTGGTTCTCCAAGCCCCTCTTCACTCCAGTTGCCTTCCTGC
CTCAGGCACAGCTTCCTCTCCCTGGAAAATCTCGTCTGGGCTACT     270
GTCTCCCCAGAATCGCCTTCACGCCTGGGGACAGCCACTGCACTC
CTGCGGCAACATTTGTTCTCTCTCCAGCCTGCGTCCTGCTCAGCA     360
GCAGCCAGTCATAGATTCCTGCTCTTCAATCAATTCGGGGGATCT
GGGCTCTCCGCCTCTGCGGCCCACACCGCAGTGCCCAAATGCCCA     450
CCACACTCCTTAGTGTCCAAGGGACCGAGAAGCCCAGTGCAAGGA
GAGCAAGTTCGTGAGTGGTAGGGATATGTGGCCATGTCCCGAGAG     540
CCACGGGGACCTCTCTACAGTCAAAAACGGGAAGTTGACCACCTG
TCACGGCTGGCAGAGGCTGGACTGGGCCGCTGGCTAGGAAGCTCT     630
CTCCCCAGCCTGTGAAAGTGCACAGGATACTGGAGCGGGCTTCCC
CAGCAGCGGATCCTCGCGTGGGTGCAGGCAAGGTCAGGTGCGCAT     720
TGTTCCCACAGAGGGAGTTCACCAGCGGAGTCAGACCCCGGGACG
TTCTGTGTGGCCGAAACCGGCTGAACGTGAACCTAGAGCAGTAAC     810
TGGCGAGCATACGATGCCGCGGAGCACACGCATGAGCATGAATAT
CTTGGTTCCGCGCTCGCAGTCCCCTCGTTCCCGCCTTGCGCTCAA     900
ACACTCAGGCTGGCGACACCCTGCACTCCAGTGTGGAAGACT
TGCGCTCCCCCTGCGGCCCAGGCGAACCCCGCTCTCCCTGCGCC     990
TCCCACCCCAGTCCTCCAACCCCATCCTCTGCCTCCCAACCTAAC
GACGTCGCTGTGGTCTGCGTCCGCCCTGACCGGCAGGTGAAAGG    1080
CGGAGCTGCAATGCCATCCCGCGGCTGTCAGGTGCCCAGGGAAGA
GTTTGGCGACAAGCAGGGCTGCGTGGATTTCGGGCAGCGCCAACT    1170
TTCTGCCTGTATGACTTTGGGCAAGTGACTTCATTCCTCTGAGCC
TGTCTTTGCACCTGCAAAGAGGGCTACGTATCCCTTCCAGGTAGA    1260
GTGAGTGCGATGAGGACCTAGTGGGTGCACAAGGGCACCAAGGCG
```

Fig. 2-2

```
CACCGATGCTCGGCAGGCCAGGGCGCGCGCTCGCTGCAAATGGAG      1350
TTCCCCTGTGCGCTCAGCTCTGCAGCTCCAAGTGCAGCCTGGAGC
GAGCCCGCCGAGCCGCGGGATCCCTCCGGGGTGGGATAAGGGAGG      1440
GGAGCCCCCGCGGCCCCCTCCCGGCCCTCGGCGCGGCCGCGTGCG
TGGTGTCATTGGCCCGGGCGGCCCGGTGGGCGGGAGGATGACATC      1530
AGCGGCAGGTTGGATTATAAAGGCGCGAGCAGAGTCACGGGCTCA
GAGCGCACCCAGCCGGCGCCGCGCAGCACTGGGACCCTGCTCGCC      1620
CTGCAGCCCAGCCAGCCTGCTCCGCATCCCCTGCTGGTCTGCCC
GCCGACCTGCGCGCCCTCGCTGCCGCCCGTGTGCGCCCCTCGACC      1710
CCAGCGGCACCATGCATCTCTCCCAGCTGCTGGCCTGCGCCCTGC
               MetHisLeuSerGlnLeuLeuAlaCysAlaLeuL

TGCTCACGCTGCTCTCCCTCCGGCCCTCCGAAGCCAAGCCCGGGG      1800
euLeuThrLeuLeuSerLeuArgProSerGluAlaLysProGlyA

CGCCGCCGAAGGTGGGTGCTGTCGTGGGGACGCCGAGCCTGGGAG
laProProLys

AGGCGTGGGAGGCTGGGGGCTTGGAGAATGCGGCGCGCAGGACCC      1890
AGGAGAGAGGGAAGGCAGGCGGCTGTCTCCTCCGAGATGCGCGTG
GGCGAGAGCCGGGGAGCCCTCGAAGCGCGGATTCGGGGGTCCACT      1980
TCTCCAGCCTCCGGAGAACATCGGCCCATGCGCAGCCCCCTACCC
CAGTGTGGCCTGCCCGGCGAGCAGCAAAGGGAGGGCAGGGGCTT      2070
CCGGAGGGAGCGGCGAAGGCGGCCGCGTGGCAGGTGGATGCGGGG
CCAAGCTGGCCGGCATCGGTGGGGCGGCTCTGGGCTTGGAGGG       2160
ACACCCCGCGCCGGCGGGCGCGTGGGCTGGAGCATCAGAGTCCC
CCGTGCTGCAGCCGCGTGTCCCTTCACCTGCCCGCTCTTTCCTCG      2250
GACAGGTCCCGCGAACCCCGCCGGCAGAGGAGCTGGCCGAGCCGC
ValProArgThrProProAlaGluGluLeuAlaGluProG
```

Fig. 2-3

```
AGGCTGCGGGCGGCGGTCAGAAGAAGGGCGACAAGGCTCCCGGGG           2340
lnAlaAlaGlyGlyGlyGlnLysLysGlyAspLysAlaProGlyG

GCGGGGGCGCCAATCTCAAGGGCGACCGGTCGCGACTGCTCCGGG
lyGlyGlyAlaAsnLeuLysGlyAspArgSerArgLeuLeuArgA

ACCTGCGCGTGGACACCAAGTCGCGGGCAGCGTGGGCTCGCCTTC           2430
spLeuArgValAspThrLysSerArgAlaAlaTrpAlaArgLeuL

TGCAAGAGCACCCCAACGCGCGCAAATACAAAGGAGCCAACAAGA
euGlnGluHisProAsnAlaArgLysTyrLysGlyAlaAsnLysL

AGGGCTTGTCCAAGGGCTGCTTCGGCCTCAAGCTGGACCGAATCG           2520
ysGlyLeuSerLysGlyCysPheGlyLeuLysLeuAspArgIleG

GCTCCATGAGCGGCCTGGGATGTTAGTGCGGCGCCCCTGGCGGC
lySerMetSerGlyLeuGlyCys***

GGTGAGTACGGCCCACCCGACGCCCAGCCCCAGCCCGGCCCGGGA           2610
CCGCCCGCCGCCCAGCCAGCCTTCGGAGGCGCGCGAGCCGCCTTT
GCTCAAGTTGTGCTAGGCGTTTGCCAGCCGCCCCCTTTATTATCC           2700
CACTTTACAGACAAAGAAAGCGAAGGATAACGTGATCGGGGAACT
TTGGCAAGGTCAGAAACGGCTCAGCCTGGTTGAACCCACCTGGCT           2790
TCTTCTGGAGAAGCAGAAACAGGCTTGGTGGTGTCTCACCCACCC
CTGAACCGTAGCTGAACTAGCAGCACTGGCCCCTATTGGCCAGCT           2880
GGTGGGGGATTGAGAGGAGATCATGGGTTTGTGGGAGCAGAGAA
GGAAGGTTACACCCACAAGTCCAGGGGACATCGATCATCTGCTGG           2970
CCACCATGCCCCTGTAGTGAGAGTAGCCCTCTGCTGGCACTGTC
AGAGCGCCCTTCTGCCTGGGACACTCCGATTCCTGTCCCTTCTCT           3060
AAACCCAGGCAGTGGGCAAACTGGTCTGTCCAGGGTCCTGAGGCA
GCTGCAGCCTGGTGGCTTCGGGGGTGAATCTCAGTGCTTGTGGCA           3150
```

Fig. 2-4

```
CTATTTCAGGGAATAGGAAAGACACTAAAGTAAATATTATTTGCC
CCAGCCTCGAACTCAACACGTCCCAGAGTCCCTCACCAACCCTGT      3240
CCCGACCCAACCGGTGCTCTGGGCTCCGTTTCTGGTGTGGGGTCT
CACCCCGCACTAGGGCTGGAAACCTCTGCCCTACCGCCACCCCT      3330
GCCGGGTGCCGCGTGGTGGTAATTTACTGCTGCAGAGAGCCTCAC
CTCTCCTCTTTCCCTCCTCTATTCCTGCCGCCTGCCCGTGCCC      3420
ACTGAATAACATCCCAGCCTCTGACATTGACAGTCATGTGCGTTA
GGATCAGGCTTACCTGGCTTTCTCGCTTTCTTGCCTCCAGCTCAG      3510
CAGCTGCCACTGCCTGTCCCACACCTTGACTGTCCCATCCCAGGC
TACGGGCAAGCTGCTGTCCTCCCCAGAAACCCTTGTCAGTGTGGA      3600
TCTTCTCCCGGAGGAAACAAGAGCGCCTGTCCAGCACACTGTCTC
TTTTTTACAGTACTGAACACTTTTTCACAGTTTGTGAACCCATTC     3690
ACCTCTCCATATTGAACAGCTTAAGGGCGAAGTGCTGGCCTAAGG
CACTCTAGGACCCACTGCACCCCGAACAGACTCGTGGAAATATTT    3780
GTCAATGACCAGAGAAACCAGCACACCCTGGCCCATGGCCACTCC
CACCTGCCCGAGGTTTTAACCAGTGCCCTTCCTCTCTTTGCAGCC    3870
AGACCTCACTCGGCTGTGGGCCTCTCCCCAGTTCTGCAAAGGCTG
TAGTTGTCTGTGATCTTGACTCTCCCTGCACAGGGAGAAGAATG     3960
ATTCTGACACTTGGGGACCAGCCTTCAGTAGCTACCCTTGGAATG
CCTTTGCTCTCTTCTCTCCTGTCTAAACAACAAAGAGACGGAGTC    4050
TGAGGCCTCAAATTTTCAGTTTGATTTAAGCATCAAGTTCAAACT
TTAGAACCTGAGCAAATGTTAGTGACTCTCCATTGGTTCGTACCT   4140
GGAATGCGCATCCCCACAGGGGCTTTGTTCTTGGGCCTGGCTGTC
TGTGGTCACCAAGTGATGGCCAAACGGGTGGTGAAAGATGCTGTG   4230
TAGGAGGAATCCACATTGTTAAGAATTC                     4258
```

Fig. 3

```
  1                                                        20
MetHisLeuSerGlnLeuLeuAlaCysAlaLeuLeuLeuThrLeuLeuSerLeuArgProSer
ATGCATCTCTCTCCCAGCTGCTGGCCTGCGCCCTGCTGCTCACGCTGCTCTCCCTCCGCCCTCC
                         30                                           40
GluAlaLysProGlyProLysValProArgThrProProAlaGluGluLeuAlaGlu
GAAGCCAAGCCCGGCCCGAAGGTCCCGCGGACCCCGCCGGCAGAGGAGCTGGCCGAG
                                       50                                           60
ProGlnAlaAlaGlyGlyGlyGlnLysLysGlyAspLysAlaProGlyGlyGlyAlaAsn
CCGCAGGCTGCGGGGGGCCAGAAGAAGGGCGACAAGGCTCCCGGGGGCGGGGCCAAT
                                       70                                           80
LeuLysGlyAspArgSerArgArgLeuLeuArgAspLeuArgValAspThrLysSerArgAlaAla
CTCAAGGGGGACCGGTCGCGCAGGCTCCTGCGGGACCTGCGCGTGGACACCAAGTCGCGGGCAGCG
                                       90                                           100
TrpAlaArgLeuLeuGlnGluHisProAsnAlaArgLysTyrLysGlyAlaAsnLysLysGly
TGGGCTCGCCTTCTGCAAGAGCACCCCAACGCGCAAATACAAAGGAGCCAACAAGAAGGGC
                                       110                                           120
LeuSerLysGlyCysPheGlyLeuLysLeuAspArgIleGlySerMetSerGlyLeuGlyCys
TTGTCCAAGGGCTGCTTCGGCCTCAAGCTGGACCGGATCGGCTCCATGAGCGGCCTGGGATGT
126
```

HUMAN CNP GENE AND PRECURSOR PROTEIN

BACKGROUND OF THE INVENTION

This invention relates to the gene of a human CNP (human C-type natriuretic peptide which is hereunder abbreviated as hCNP), as well as the hCNP precursor protein (prepro hCNP) that is encoded by said gene.

In recent years, various peptides collectively referred to as "natriuretic peptides" (NP) have been isolated from the atria and brains of various animals. Today those NPs can be classified into three types, A-type natriuretic peptide (ANP), B-type natriuretic peptide (BNP) and C-type natriuretic peptide (CNP), depending on similarities in the primary amino acid sequence and the structure of their precursors. Among the three types, ANP and BNP were first isolated and identified from the atrium and brain and hence are sometimes called "atrial natriuretic peptide" and "brain natriuretic peptide", respectively (Matsuo, H. and Nakazato, H., Endocrinol. Metab. Clin. North Am., 16, 43, 1987; Sudoh, T. et al., Nature, 332, 78, 1988). However, it is known today that ANP occurs not only in the atrium but also in the brain and that BNP occurs not only in the brain but also in the atrium. Further, both ANP and BNP exhibit significant natriuretic and hypotensive actions, so it has become clear that each of these peptides works not only as a hormone to be secreted from the atrium into blood but as a nerve transmitter in the brain, in either case helping regulate the homeostatic balance of body fluid volume and blood pressure in mammals.

The CNP has very recently been isolated and identified from porcine brain by Sudoh et al. as a third type of NP that is assignable to neither ANP nor BNP (Sudoh, T. et al., Biochem. Biophys. Res. Commun., 168, 863, 1990). The first discovered CNP consisted of 22 amino acid residues (this peptide is hereunder abbreviated as "pCNP-22"). Like ANP and BNP, CNP contained two cysteine residues which formed an intramolecular disulfide bond, producing a ring structure composed of 17 amino acid residues. Further, the primary amino acid sequence forming that ring structure in pCNP-22 was found to be highly homologous to that in ANP and BNP.

However, pCNP-22 differs from ANP and BNP in that the latter have several amino acid residues additionally attached to the C-terminus of the ring structure whereas no such "tail structure" is present in pCNP-22. In other words, the C-terminus of pCNP-22 is terminated with a cysteine residue. On the basis of these facts, it has been found that the structure of pCNP-22 is similar to but clearly distinguishable from those of ANP and BNP. In addition, pCNP-22 exhibited natriuretic and hypotensive actions and it was also found to display a higher activity than ANP and BNP in relaxant activity tests on chick rectal samples. From these observations, pCNP-22 was found to be an NP assignable to a new type, the peptides of which were named "CNPs".

Following pCNP-22, a second peptide assignable as CNP was isolated and identified from porcine brain by the present inventors. The peptide was found to consist of 53 amino acid residues with pCNP-22 present at the C-terminus (this peptide is hereunder abbreviated as pCNP-53). In other words, pCNP-53 was found to be a peptide that had 31 more amino acid residues attached to the N-terminus of pCNP-22. Interestingly enough, pCNP-53 has been found to occur in a greater amount than pCNP-22 in porcine brain (commonly assigned Japanese Patent Application No. 186582/1990).

Another very recent study succeeded in identifying the structure of the precursor of pCNP-22 and pCNP-53 by gene analysis and this helped unravel the mechanism behind the biosynthesis of those peptides (commonly assigned Japanese Patent Application No. 186583/1990). The present inventors isolated and identified a porcine chromosomal gene and cDNA coding for pCNP-22 and pCNP-53; by their analysis, the structure of the porcine CNP precursor protein (prepro pCNP) was unravelled; at the same time, it was found that each of pCNP-22 and pCNP-53 was first translated from mRNA as a prepro pCNP composed of 126 amino acid residues and that the signal peptide present in the N-terminal region of the precursor protein was then cleaved in the process of secretion to be converted to pro pCNP, which was further cleaved specifically with processing enzymes and converted to pCNP-53 or pCNP-22 as appropriate. On the basis of these observations, it has been found that as in the case of ANP and BNP, both pCNP-22 and pCNP-53 are secretory peptides that are biosynthesized from a common precursor protein (prepro pCNP).

However, in sharp contrast to the peptides assignable to ANP and BNP which have been found by previous studies to work not only as hormones to be secreted from the atrium into blood but also as nerve transmitters in the brain, thereby regulating the homeostatic balance of body fluid volume and blood pressure, CNP remains unclear in many points as regards details of its distribution in vivo and physiological actions.

As for ANP and BNP, their structures have been established in humans and the efforts to apply them as pharmaceuticals are under way. However, as of today, the structure of CNP has not been identified in humans.

SUMMARY OF THE INVENTION

The present invention has been accomplished under these circumstances and has as an object identifying the structures of CNPs in humans (hCNP), particularly those of human CNPs that correspond to pCNP-22 and pCNP-53, as well as the structure of their precursor protein which corresponds to prepro pCNP in porcine.

BRIEF DESCRIPTION OF THE DRAWINGS

FIG. 1 shows the restriction enzyme map for hgEco-2 and hgEco-1, as well as the strategy for base sequence determination;

FIG. 2 shows DNA base sequence of hgEco-1 coding for the hCNP precursor protein, as well as the amino acid sequence of hCNP precursor protein coded by the exons in the structural gene region; (See SEQ ID NOS: 5 and 6, respectively) and FIG. 3 shows the whole base sequence of hCNP cDNA, as well as the amino acid sequence of the hCNP precursor protein coded by it. (See SEQ ID NOS: 8 and 7, respectively)

DETAILED DESCRIPTION OF THE INVENTION

Noting that the amino acid sequence of ANP and the base sequence of the gene encoding it are both retained with high homology across animal species, the present inventors thought that there would be a high likelihood of the same situation occurring in CNP. Further noting that CNP occurs in a much smaller amount in porcine brain than ANP and BNP do and that the brain tissue for the production of those peptides is yet to be identified, the present inventors thought it difficult to isolate and identify the CNP peptide directly from a human brain and to isolate and analyze the cDNA for identifying human CNP. Based on these assumptions, the present inventors projected a program in which the human CNP gene was isolated using as a probe the previously obtained porcine CNP gene or cCNP and the isolated human CNP gene was analyzed to identify the structure of the human CNP precursor protein as well as the structures of human CNPs that correspond to pCNP-53 and pCNP-22.

In accordance with this program, the present inventors first cut a DNA fragment of ca. 70 based (pC cDNA) from pCNP cDNA (see commonly assigned Japanese Patent Application No. 186583/1990) by processing with a restriction enzyme DdeI and used this fragment as a probe. The probe may also be synthesized chemically. Using this probe, the present inventors screened a human chromosomal gene library (λ-phage vector incorporating a human chromosomal gene fragment). The human chromosomal gene library can be readily prepared by one skilled in the art or, alternatively, it is commercially available from Clonetech Co. As a result, a clone hybridizing pC cDNA was obtained. Analysis of this clone (λhCNP2) showed that it harbored ca. 15 kbp of the human chromosomal gene and that an EcoRI DNA fragment (hgEco-2) composed of ca. 2 kbp of that 15 kbp hybridized with the pC cDNA probe. When this hgEco-2 composed of ca. 2 kbp was analyzed, it became apparent that this DNA fragment contained part of the hCNP gene (for the restriction enzyme map for hgEco-2 and the strategy for base sequence determination, see FIG. 1).

In the next step, with a view to identifying the whole structure of the hCNP precursor protein, the present inventors screened the human chromosomal gene library again using hgEco-2 as a probe. As a result, a clone that hybridized with the hgEco-2 probe was obtained. Analysis of this clone (λhCNP1) confirmed that it contained a human chromosomal gene of 15 kbp and more and that an EcoRI fragment (hgEco-1) of that clone that was composed of ca. 4 kbp hybridized with the hgEco-2 probe. The present inventors then constructed a restriction enzyme map for the hgEco-1 fragment and compared with the map already constructed for hgEco-2 (see FIG. 1). As a result, it became clear that hgEco-1 was a DNA that had a human chromosomal gene of ca. 2 kpb additionally attached to the 5' side of hgEco-2. Based on this finding, the present inventors determined the base sequence of the DNA fragment of interest (for the strategy for determining the base sequence of hgEco-1, see FIG. 1). As a result, it was found that as shown in FIG. 2, the hgEco-1 contained not only a structural gene coding for the whole amino acid sequence of the human CNP precursor protein but also the promoter region of the human CNP gene.

First, as for the promoter region, a TATA box that was shared by the promoter regions of eukaryotic genes was present in positions 1546–1551 of the DNA base sequence shown in FIG. 2 and it was also found that two GC boxes and one Y box, both of which would presumably take part in the control of gene expression, were present upstream of the TATA box. Based on these facts, the present inventors concluded that the region of interest was the promoter region of the CNP precursor gene.

As for the structural gene region, ATG was present in positions 172–174 of the base sequence downstream (on the 3' side) of the TATA box. Since this ATG was the first methionine codon that appeared downstream (on the 3' side) of the TATA box and since the base sequence around that codon was in agreement with the consensus sequence of a translation initiation codon, A/G NNATG (N denotes either one of A, T, G and C), which is known to exist in eukaryotes, the present inventors estimated that the ATG of interest would be a translation initiation codon for the human CNP precursor. If this ATG is assumed to be a translation initiation codon, comparison with the already identified structure of the porcine CNP chromosomal gene shows that the area up to the codon (AAG) of the lysine residue present in positions 1809–1811 of the base sequence corresponds to the first exon. A similar comparison also shows that the second exon starts with the codon (GTC) of the valine residue present in positions 2256–2258 of the base sequence. The first analyzed hgEco-2 is a DNA fragment coding for the area of the second exon in position 2286 onward of the base sequence. These facts are also supported by the following: base sequences similar to C/A AGGT and A/G AGT which are known as the consensus sequences of a splicing donor are present in the neighborhood of position 1810 of the base sequence; and a base sequence similar to (Py)nNC/T AGG (Py denotes the pyridine residue, and N denotes either one of A, T, C and G) which is known as the consensus sequence of a splicing acceptor is present on the 5' side of position 2256 of the base sequence. Based on these observations, the present inventors presumed that the DNA region in positions 1812–2255 of the base sequence was an intron and that said intron could be removed by splicing during the formation of a mature mRNA coding for the hCNP precursor protein. In other words, it became clear that the hCNP precursor protein was coded by the first exon which started at position 1722 of the base sequence and which ended at position 1811 and also by the second exon which started at position 2256 and that said precursor protein was a polypeptide that was totally composed of 126 amino acid residues as in porcine.

The thus identified hCNP precursor protein (which is hereunder referred to as the "prepro hCNP") was compared for its primary amino acid sequence with the pCNP precursor protein. The two precursor proteins were found to be identical except for the difference in five positions of the amino acid sequence (positions 37, 40, 56, 90 and 101 of the primary amino acid sequence of prepro hCNP shown in FIG. 3). It was particularly interesting that the following two amino acid sequences were completely the same in humans and pigs: the primary amino acid sequence of the signal peptide that existed in the N-terminal region of prepro CNP which was already found to take part in the secretion of the CNP precursor protein in the mechanism of biosynthesis of porcine CNP; and the amino acid sequence in areas near the N-terminus of CNP-22 and CNP-53 that would be recognized and cleaved by processing enzymes during the formation of CNP-22 and CNP-53 from prepro CNP.

With the above-discussed facts taken into consideration, the human CNP is presumably biosynthesized by the following pathway which is similar to that associated with porcine. First, prepro hCNP composed of 126 amino acid residues is translated from mRNA. Then, the signal peptide present in the N-terminal region of the prepro hCNP is cleaved for conversion to pro hCNP in the process of secretion. Further, the pro hCNP is cleaved by processing enzymes at specific positions (between positions 73 and 74 of the primary amino acid sequence that is shown in FIG. 3 and between positions 104 and 105 of the same sequence) to be converted to human CNP-53 (positions 74–126 of the primary amino acid sequence shown in FIG. 3) that corresponds to pCNP-53, as well as to human CNP-22 (positions 105–126 of the same sequence) that corresponds to pCNP-22. As for hCNP-22, its primary amino acid sequence is completely identical to that of pCNP-22, so there is no doubt that it will exhibit the same physiological activities as does pCNP-22 (e.g. natriuretic and hypotensive actions).

On the other hand, the amino acid sequence of hCNP-53 differs from that of pCNP-53 in two positions (positions 90 and 101 of the primary amino acid sequence shown in FIG. 3), so hCNP-53 is a novel peptide and its physiological actions have not been known. Hence, the present inventors synthesized hCNP-53 chemically and examined the physiological activities of that novel peptide. As a result, it was found that hCNP-53 exhibited a chick rectum relaxant action; at the same time, it showed definite natriuretic and hypotensive actions when administered to rats.

In summary, the present inventors isolated a chromosomal gene coding for the hCNP precursor protein and analyzed it to identify its primary amino acid sequence. As a result, they successfully identified the structures of human CNPs (hCNP-22 and hCNP-53) corresponding to pCNP-22 and pCNP-53. At the same time, they synthesized hCNP-53 chemically and verified its physiological activities. The present invention has been accomplished under these circumstances.

It should be noted here that if the hCNP chromosomal gene of the present invention is transduced into a suitable mammalian cell (e.g. COS cell derived from monkey kidney cells) either directly or as it is linked to an area downstream of a suitable promoter (e.g. the initial promoter of SV 40), hCNP cDNA can be obtained and this fact is within the scope of obviousness (see commonly assigned Japanese Patent Application No. 186583/1990).

The whole base sequence of the thus obtained hCNP cDNA and the primary amino sequence of the hCNP precursor protein coded by said cDNA are shown in FIG. 3.

The following examples are provided for the purpose of further illustrating the present invention but are in no way to be taken as limiting.

EXAMPLE 1

Preparation of DNA probe (PC cDNA)

The DNA probe (pC cDNA) to be used for cloning a chromosomal gene that encoded the human CNP precursor protein was prepared by the method consisting of cleaving the porcine CNP cDNA (see commonly assigned Japanese Patent Application No. 186583/1990) with a restriction enzyme DdeI, isolating a DNA fragment of ca. 700 bp, then marking the DNA with [$\alpha$-$^{32}$P] dCTP by nick translation.

EXAMPLE 2

Isolation of chromosomal gene coding for part of the human CNP precursor protein E. coli strain K12 derived LE 392 was infected with a human chromosomal gene phage DNA library stored at 4° C. The cells were plated on an LB medium (10 g, bactotryptone; 5 g, yeast extract; 5 g, NaCl; 1.5%, bactoagar; total volume, 1 l) and cultivated overnight at 37° C. The plate was cooled at 4° C. for 30 min and a nitrocellulose filter (product of Shleicher & Schnell Co.) was left to stand on the phage plaque for 5 minutes. Subsequently, the filter was stripped from the plate, dried with air, immersed in an alkaline denaturation solution (0.5 M NaOH and 1.5 M NaCl) for 1 minute, and then immersed in a neutralizing solution (0.5 M Tris-HCQ; pH 7.0; 1.5 M NaCl) for 1 minute. Thereafter, the nitrocellulose filter was rinsed with a 3×SSC solution (20× SSC NaCl, 175.3 g; trisodium citrate, 88.2 g; total volume, 1 l), dried with air and heat-treated under vacuum at 80° C. for 120 min.

Using the thus prepared nitrocellulose filter, plaque hybridization was performed under the following conditions. First, a prehybridization solution [3×SSC; 1×Denhardt's solution (consisting of albumin, polyvinyl pyrrolidone and Ficoll, each weighing 0.2 mg/ml); salmon sperm DNA, 50 µg/ml; 0.1% SDS] was added to the nitrocellulose filter and prehybridization was conducted at 60° C. for 3 hours. Then, using $10^6$ cpm of the pC cDNA probe and 1 ml of the prehybridization solution for two sheets of the nitrocellulose filter, hybridization was performed overnight at 60° C. Subsequently, the filter was washed three times with a 3×SSC solution containing 0.1% SDS, each washing done at 60° C. for 30 minutes; the washed filter was dried with air and subjected to autoradiography at −80° C. for 24 h. By screening ca. $2×10^5$ clones in this way, one clone hybridizing with the pC cDNA probe was obtained. This clone was named "λhCNP 2" and subjected to analyses in the subsequent stages.

EXAMPLE 3

Analysis of λhCNP 2 phage and determination of its DNA base sequence

A. Analysis of λhCNP 2 phage DNA

DNA was prepared from λhCNP 2 phage in the usual manner. Subsequently, the phage DNA was cleaved with a restriction enzyme EcoRI and the resulting DNA fragment was separated and analyzed by electrophoresis on an agarose gel. The λhCNP 2 was found to be a phage containing a ca. 15-kbp human chromosomal gene. Analysis by Southern blotting using the pC cDNA probe showed the EcoRI fragment of hCNP 2 (hgEco-2) having a length of ca. 2 kbp hybridized with the pC cDNA probe.

B. Determining the base sequence of hgEco-2 DNA fragment

In order to determine the base sequence of the hgEco-2 DNA fragment, the latter was first subcloned in a plasmid vector pUC 118 (Takara Shuzo Co., Ltd.) at the EcoRI site to prepare pUC hCNP 2. The pUC hCNP 2 was then cleaved with a suitable restriction enzyme and the resulting DNA fragment was subcloned in M13 phage. The base sequence of the hgEco-2 DNA fragment was determined by the dideoxy method.

As a result, it was found that the DNA fragment of interest encoded part of the human CNP gene.

EXAMPLE 4

Isolation of chromosomal gene coding for the entire region of human CNP precursor protein Using the nitrocellulose filter conditioned by the method described in Example 1, plaque hybridization was performed under the conditions described below. The probe to be used was prepared by marking the hCNP 2 derived hgEco-2 (ca. 2 kbp) with [$\alpha$-$^{32}$P] dCTP by nick translation. The thus prepared probe is hereunder designated hgEco-2 DNA.

First, a prehybridization solution [3×SSC; 1×Denhardt's solution (consisting of albumin, polyvinyl pyrrolidone and Ficoll, each weighing 0.2 mg/ml); salmon sperm DNA 50 µg/ml; 0.1% SDS] was added to the nitrocellulose filter and prehybridization was conducted at 65° C. for 3 hours. Then, using $10^6$ cmp of the hgEco-2 DNA probe and 1 m of the prehybridization solution for two sheets of the nitrocellulose filter, hybridization was performed overnight at 65° C. Subsequently, the filter was washed three times with a 3×SSC solution containing 0.1% SDS, each washing done at 65° C. for 30 minutes; the washed filter was dried with air and subjected to autoradiography at −80° C. for 24 h. By screening ca. $5×10^5$ clones in this way, five clones hybridizing with the hgEco-2 DNA probe were obtained. One of those clones was named "λhCNP1" and subjected to analyses in the subsequent stages.

EXAMPLE 5

Analysis of λhCNP1 phage DNA and determination of its DNA base sequence

A. Analysis of λhCNP1 phage DNA

DNA was prepared from the λhCNP1 phage in the usual manner. Subsequently, the phage DNA was cleaved with a restriction enzyme EcoRI and the resulting DNA fragment was separated and analyzed by electrophoresis on an agarose gel. As a result, the λhCNP1 was found to be a phage containing a human chromosomal gene of ca. 15 kbp or more. Analysis by Southern blotting using the hgEco-2 DNA probe showed that the EcoRI DNA fragment (hgEco-1) of ca. 4 kbp hybridized with the hgEco-2 DNA probe. Hence, the base sequence of this DNA fragment which hybridized with the hgEco-2 DNA fragment was determined by the following method.

B. Determining the base sequence of hgEco-1 DNA fragment

In order to determine the base sequence of the hgEco-1 DNA fragment, the latter was first subcloned in a plasmid vector pUC 118 (Takara Shuzo Co., Ltd.) at the EcoRI site to prepare pUC CNP1. The pUC CNP1 was then cleaved with a suitable restriction enzyme and the resulting DNA fragment was subcloned in M13 phage. The base sequence of the DNA fragment of interest was determined by the dideoxy method. The region of the base sequence determined by the method described above is shown by solid arrows in FIG. 1.

In a separate step for determining the base sequence of the lower strand of the hgEco-1 DNA fragment (hgEco-1), the latter was first subcloned in a phage vector M13 mp18 at the EcoRI site to prepare M13 hCNP1. Then, with this M13 hCNP1 used as a template, the base sequence of the DNA fragment of interest was determined by the dideoxy method using a universal primer and the oligonucleotide primer that was synthesized chemically on the basis of the already determined base sequence. The region thus determined is shown by dashed arrows in FIG. 1. The base sequence determined by the method described above was combined with the base sequence of the hgEco-2 DNA fragment to complete the whole base sequence of the hgEco-1 DNA fragment. The completed base sequence and the amino acid sequence to be coded in the exon site as predictable from said base sequence are shown in FIG. 2.

EXAMPLE 6

Chemical synthesis of hCNP-53

The hCNP-53 was synthesized by a solid-phase method with a peptide synthesizer of Applied Biosystems Co. It was thereafter deprotected with hydrogen fluoride to form an intramolecular S—S bond, followed by purification.

The results of amino acid sequencing of the final pure product and the data of amino acid analysis are shown in Tables 1 and 2, respectively. Those results and data proved positively that the chemically synthesized hCNP-53 was exactly the intended product. Table 1 shows the yields of PTH-amino acids as obtained for successive cycles of analysis on the chemically synthesized hCNP-53 by the Edman method. In Table 1, each amino acid is designated by a single letter. Table 2 shows the data of amino acid analysis on the chemically synthesized hCNP-53.

TABLE 1

Amino Acid Sequence Analysis of Synthetic Human CNP-53

| Cycle No. | | | Cycle No. | | |
|---|---|---|---|---|---|
| 1 | D | 349.8 pmol | 28 | A | 1621.0 |
| 2 | L | 4000.6 | 29 | N | 418.3 |
| 3 | R | 105.9 | 30 | K | 1910.6 |
| 4 | V | 3060.8 | 31 | K | 1164.7 |
| 5 | D | 292.0 | 32 | G | 771.0 |
| 6 | T | 851.1 | 33 | L | 1277.0 |
| 7 | K | 2860.4 | 34 | S | 159.7 |
| 8 | S | 595.3 | 35 | K | 1204.8 |
| 9 | R | 290.6 | 36 | G | 552.8 |
| 10 | A | 2761.5 | 37 | C | ND |
| 11 | A | 2714.6 | 38 | F | 998.2 |
| 12 | W | 1038.4 | 39 | G | 668.2 |
| 13 | A | 2386.8 | 40 | L | 959.6 |
| 14 | R | 151.6 | 41 | K | 634.2 |
| 15 | L | 2628.7 | 42 | L | 1251.3 |
| 16 | L | 2701.2 | 43 | D | 141.1 |
| 17 | Q | 762.3 | 44 | R | 339.1 |
| 18 | E | 418.7 | 45 | I | 778.9 |
| 19 | H | 71.0 | 46 | G | 702.7 |
| 20 | P | 758.0 | 47 | S | 163.2 |
| 21 | N | 478.6 | 48 | M | 420.9 |
| 22 | A | 1322.9 | 49 | S | 68.8 |
| 23 | R | 138.9 | 50 | G | 430.1 |
| 24 | K | 1176.9 | 51 | L | 408.6 |
| 25 | Y | 678.9 | 52 | G | 223.7 |
| 26 | K | 1204.6 | 53 | C | ND |
| 27 | G | 1674.0 | | | |

TABLE 2

Amino Acid Composition Analysis of Synthetic Human CNP-53

| Amino acid | Found | Calculated |
|---|---|---|
| Asx | 4.95 | 5 |
| Thr | 0.92 | 1 |
| Ser | 3.59 | 4 |
| Glx | 2.06 | 2 |
| Gly | 7.04 | 7 |
| Pro | 1.01 | 1 |
| Ala | 4.90 | 5 |
| 1/2Cys | 1.21 | 2 |
| Val | 0.97 | 1 |
| Met | 0.97 | 1 |
| Ile | 0.99 | 1 |
| Leu | 7 | 7 |
| Tyr | 0.97 | 1 |
| Phe | 1.02 | 1 |
| Lys | 6.92 | 7 |
| His | 0.97 | 1 |
| Trp | ND | 1 |
| Arg | 5.04 | 5 |

EXAMPLE 7

Measurement of the Physiological Activities of hCNP-53

A. Chick rectum relaxant activity of hCNP-53

A chick rectum relaxant activity measurement was conducted in accordance with the method of Currie et al. described in Nature, 221, 1–13, 1983. The $EC_{50}$ of hCNP-53 was found to be 0.87±0.1 nM which was about three times as high as the activity of α-ANP.

B. Natriuretic and hypotensive actions of hCNP-53

The natriuretic and hypotensive actions of hCNP-53 were measured in accordance with the method of DeBold et al.

described in Life Sci., 28, 89–94, 1981. As a result, it was found that hCNP-53, when administered in a dose of 100 nmol/kg, increased the urine clearance by 2.5 times while reducing the blood pressure by 10%.

As described on the foregoing pages, the present inventors isolated part of the hCNP gene from a human chromosomal gene library using pCNP cDNA as a probe. With the isolated hCNP gene being used as a probe, a gene coding for the whole region of the hCNP precursor was successfully isolated. The isolated gene also contained the promoter region of hCNP. As a result, it was verified that a gene coding for CNP also existed in humans as well as in pigs. Further, the whole structure of the hCNP precursor protein was determined. As in pigs, the hCNP precursor protein was composed of 126 amino acid residues and contained at the C-terminus the amino acid sequences that corresponded to pCNP-53 and pCNP-22 isolated from porcine brain. Since the amino acid sequences of those peptides at the processing site were in complete agreement between porcine and human, it is predicted that those peptides would also be biosynthesized in humans through a pathway similar to that involved in pigs and that they would work as hormones or nerve transmitters that regulate the homeostatic balance of body fluid volume and blood pressure in vivo.

What is worth particular note in the present invention is that the hCNP-53 was found to be structurally different from pCNP-53 in two positions of the amino acid sequence. The present inventors therefore synthesized hCNP-53 chemically and checked its physiological activities in terms of chick rectum relaxant action, as well as natriuretic and hypotensive actions. As a result, hCNP-53 proved to be a physiologically active peptide. This will bear great importance on the application of peptides of the CNP family to pharmaceuticals. For instance, if pCNP-53 which is structurally different from hCNP-53 is used as a pharmaceutical, it will probably be recognized as foreign matter in the human body to cause antibody production. As a consequence, the activity of pCNP-53 may be neutralized or nephrotoxicity may be caused by an antigen-antibody complex. Further, pCNP-53 may have less affinity for the CNP receptor of human cells than hCNP-53 does and, in that case, the action per se of pCNP-53 may be attenuated. These problems are absent from hCNP-53 and the same is true for other peptides that can be biosynthesized from the hCNP precursor protein [between positions 24 and 102 of the primary amino acid sequence of prepro hCNP, there are at least 9 lysine residues (in positions 24, 30, 51, 52, 55, 65, 89, 97 and 99) and at least 8 arginine residues (in positions 33, 68, 70, 73, 76, 82, 87 and 96) and pro hCNP can be cleaved by processing enzymes in vivo at specific positions on the C-terminal side of those basic amino acid residues to increase the likelihood that there exist in vivo those peptides which have additional amino acids attached to the N-terminus of hCNP-22 and hCNP-53].

It has also been found that the gene of the hCNP precursor protein shown in FIG. 2 contains not only the structural gene region coding for that protein but also the promoter region which expresses that structural gene. By linking, for example, the gene of CAT (chloramphenicol acetyl transferase) to an area downstream of this promoter region and by transducing the combination into a suitable human cell, it becomes possible to closely study the mechanism behind the regulation of hCNP expression.

Hence, the information obtained by the present invention concerning the chromosomal gene of the hCNP precursor protein and its primary amino acid sequence will make great contributions not only to future studies for unravelling the mechanism behind the biosynthesis and physiological actions of CNPs in humans but also to the efforts to establish pharmaceutical applications of peptides assignable to the CNP family.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 126 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met His Leu Ser Gln Leu Leu Ala Cys Ala Leu Leu Leu Thr Leu
1               5                   10                  15

Leu Ser Leu Arg Pro Ser Glu Ala Lys Pro Gly Ala Pro Pro Lys
                20                  25                  30

Val Pro Arg Thr Pro Pro Ala Glu Glu Leu Ala Glu Pro Gln Ala
                35                  40                  45

Ala Gly Gly Gly Gln Lys Lys Gly Asp Lys Ala Pro Gly Gly Gly
                50                  55                  60

Gly Ala Asn Leu Lys Gly Asp Arg Ser Arg Leu Leu Arg Asp Leu
```

```
                        65                  70                  75
Arg Val Asp Thr Lys Ser Arg Ala Ala Trp Ala Arg Leu Leu Gln
                    80                  85                  90

Glu His Pro Asn Ala Arg Lys Tyr Lys Gly Ala Asn Lys Lys Gly
                95                  100                 105

Leu Ser Lys Gly Cys Phe Gly Leu Lys Leu Asp Arg Ile Gly Ser
                    110                 115                 120

Met Ser Gly Leu Gly Cys
                    125

(2) INFORMATION FOR SEQ ID NO:2:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asp Leu Arg Val Asp Thr Lys Ser Arg Ala Ala Trp Ala Arg Leu
1               5                  10                  15

Leu Gln Glu His Pro Asn Ala Arg Lys Tyr Lys Gly Ala Asn Lys
                20                  25                  30

Lys Gly Leu Ser Lys Gly Cys Phe Gly Leu Lys Leu Asp Arg Ile
                35                  40                  45

Gly Ser Met Ser Gly Leu Gly Cys
                50

(2) INFORMATION FOR SEQ ID NO:3:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

ATGCATCTCT CCCAGCTGCT GGCCTGCGCC CTGCTGCTCA CGCTGCTCTC CCTCCGGCCC    60

TCCGAAGCCA AGCCCGGGGC GCCGCCGAAG GTCCCGCGAA CCCCGCCGGC AGAGGAGCTG   120

GCCGAGCCGC AGGCTGCGGG CGGCGGTCAG AAGAAGGGCG ACAAGGCTCC CGGGGGCGGG   180

GGCGCCAATC TCAAGGGCGA CCGGTCGCGA CTGCTCCGGG ACCTGCGCGT GGACACCAAG   240

TCGCGGGCAG CGTGGGCTCG CCTTCTGCAA GAGCACCCCA ACGCGCGCAA ATACAAAGGA   300

GCCAACAAGA AGGGCTTGTC CAAGGGCTGC TTCGGCCTCA AGCTGGACCG AATCGGCTCC   360

ATGAGCGGCC TGGGATGT                                                378

(2) INFORMATION FOR SEQ ID NO:4:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:
```

```
GACCTGCGCG TGGACACCAA GTCGCGGGCA GCGTGGGCTC GCCTTCTGCA AGAGCACCCC    60

AACGCGCGCA AATACAAAGG AGCCAACAAG AAGGGCTTGT CCAAGGGCTG CTTCGGCCTC   120

AAGCTGGACC GAATCGGCTC CATGAGCGGC CTGGGATGT                          159
```

(2) INFORMATION FOR SEQ ID NO:5:

(i) SEQUENCE CHARACTERISTICS:
        (A) LENGTH: 4258 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GAATTCCTGT TTCCTAAGCA AAGTGACCTG TGTAGTGGTT GCTCCAATGT TGTGAGTCAG    60

GGTATGAGAG TGGGAAGGGG TAGCCTGAGA AAGGTGCCGA CAGAGCAGAC CATGATGCGG   120

CCGCCTTAGC AGCTCTGGGA CCAGGCTCAC TACCACGGAG GGAAGAGGGA GGCTTGGAGG   180

GAACCTGGTT CTCCAAGCCC CTCTTCACTC CAGTTGCCTT CCTGCCTCAG GCACAGCTTC   240

CTCTCCCTGG AAAATCTCGT CTGGGCTACT GTCTCCCCAG AATCGCCTTC ACGCCTGGGG   300

ACAGCCACTG CACTCCTGCG GCAACATTTG TTCTCTCTCC AGCCTGCGTC CTGCTCAGCA   360

GCAGCCAGTC ATAGATTCCT GCTCTTCAAT CAATTCGGGG GATCTGGGCT CTCCGCCTCT   420

GCGGCCCACA CCGCAGTGCC CAAATGCCCA CCACACTCCT TAGTGTCCAA GGGACCGAGA   480

AGCCCAGTGC AAGGAGAGCA AGTTCGTGAG TGGTAGGGAT ATGTGGCCAT GTCCCGAGAG   540

CCACGGGGAC CTCTCTACAG TCAAAAACGG GAAGTTGACC ACCTGTCACG GCTGGCAGAG   600

GCTGGACTGG GCCGCTGGCT AGGAAGCTCT CTCCCCAGCC TGTGAAAGTG CACAGGATAC   660

TGGAGCGGGC TTCCCCAGCA GCGGATCCTC GCGTGGGTGC AGGCAAGGTC AGGTGCGCAT   720

TGTTCCCACA GAGGGAGTTC ACCAGCGGAG TCAGACCCCG GGACGTTCTG TGTGGCCGAA   780

ACCGGCTGAA CGTGAACCTA GAGCAGTAAC TGGCGAGCAT ACGATGCCGC GGAGCACACG   840

CATGAGCATG AATATCTTGG TTCCGCGCTC GCAGTCCCCT CGTTCCCGCC TTGCGCTCAA   900

ACACTCAGGC TGGCGACACC CCTGCACTCT CCAGTGTGGA AGACTTGCGC TCCCCCCTGC   960

GGCCCAGGCG AACCCCGCTC TCCCTGCGCC TCCCACCCCA GTCCTCCAAC CCCATCCTCT  1020

GCCTCCCAAC CTAACGACGT CGCTGTGGTC TGCGTCCCGC CCTGACCGGC AGGTGAAAGG  1080

CGGAGCTGCA ATGCCATCCC GCGGCTGTCA GGTGCCCAGG GAAGAGTTTG GCGACAAGCA  1140

GGGCTGCGTG GATTTCGGGC AGCGCCAACT TTCTGCCTGT ATGACTTTGG GCAAGTGACT  1200

TCATTCCTCT GAGCCTGTCT TTGCACCTGC AAAGAGGGCT ACGTATCCCT TCCAGGTAGA  1260

GTGAGTGCGA TGAGGACCTA GTGGGTGCAC AAGGGCACCA AGGCGCACCG ATGCTCGGCA  1320

GGCCAGGGCG CGCGCTCGCT GCAAATGGAG TTCCCCTGTG CGCTCAGCTC TGCAGCTCCA  1380

AGTGCAGCCT GGAGCGAGCC CGCCGAGCCG CGGGATCCCT CCGGGGTGGG ATAAGGGAGG  1440

GGAGCCCCCG CGGCCCCCTC CCGGCCCTCG GCGCGGCCGC GTGCGTGGTG TCATTGGCCC  1500

GGGCGGCCCG GTGGGCGGGA GGATGACATC AGCGGCAGGT TGGATTATAA AGGCGCGAGC  1560

AGAGTCACGG GCTCAGAGCG CACCCAGCCG GCGCCGCGCA GCACTGGGAC CCTGCTCGCC  1620

CTGCAGCCCA GCCAGCCTGC TCCGCATCCC CCTGCTGGTC TGCCCGCCGA CCTGCGCGCC  1680

CTCGCTGCCG CCCGTGTGCG CCCCTCGACC CCAGCGGCAC CATGCATCTC TCCCAGCTGC  1740

TGGCCTGCGC CCTGCTGCTC ACGCTGCTCT CCCTCCGGCC CTCCGAAGCC AAGCCCGGGG  1800
```

```
CGCCGCCGAA GGTGGGTGCT GTCGTGGGGA CGCCGAGCCT GGGAGAGGCG TGGGAGGCTG 1860

GGGGCTTGGA GAATGCGGCG CGCAGGACCC AGGAGAGAGG GAAGGCAGGC GGCTGTCTCC 1920

TCCGAGATGC GCGTGGGCGA GAGCCGGGGA GCCCTCGAAG CGCGGATTCG GGGGTCCACT 1980

TCTCCAGCCT CCGGAGAACA TCGGCCCATG CGCAGCCCCC TACCCCAGTG TGGCCTGCCC 2040

GGCGAGCAGC AAAGGGAGGG CAGGGGGCTT CCGGAGGGAG CGGCGAAGGC GGCCGCGTGG 2100

CAGGTGGATG CGGGGCCAAG CTGGCCGGCA TCGGTGGGGG CGGCTCTGGG CTTGGGAGGG 2160

ACACCCCGCG CCGGCGGGCG CGTGGGGCTG GAGCATCAGA GTCCCCCGTG CTGCAGCCGC 2220

GTGTCCCTTC ACCTGCCCGC TCTTTCCTCG GACAGGTCCC GCGAACCCCG CCGGCAGAGG 2280

AGCTGGCCGA GCCGCAGGCT GCGGGCGGCG GTCAGAAGAA GGGCGACAAG GCTCCCGGGG 2340

GCGGGGCGC CAATCTCAAG GGCGACCGGT CGCGACTGCT CCGGGACCTG CGCGTGGACA 2400

CCAAGTCGCG GGCAGCGTGG GCTCGCCTTC TGCAAGAGCA CCCCAACGCG CGCAAATACA 2460

AAGGAGCCAA CAAGAAGGGC TTGTCCAAGG GCTGCTTCGG CCTCAAGCTG GACCGAATCG 2520

GCTCCATGAG CGGCCTGGGA TGTTAGTGCG GCGCCCCCTG GCGGCGGTGA GTACGGCCCA 2580

CCCGACGCCC AGCCCCAGCC CGGCCCGGGA CCGCCCGCCG CCCAGCCAGC CTTCGGAGGC 2640

GCGCGAGCCG CCTTTGCTCA AGTTGTGCTA GGCGTTTGCC AGCCGCCCCC TTTATTATCC 2700

CACTTTACAG ACAAAGAAAG CGAAGGATAA CGTGATCGGG GAACTTTGGC AAGGTCAGAA 2760

ACGGCTCAGC CTGGTTGAAC CCACCTGGCT TCTTCTGGAG AAGCAGAAAC AGGCTTGGTG 2820

GTGTCTCACC CACCCCTGAA CCGTAGCTGA ACTAGCAGCA CTGGCCCCTA TTGGCCAGCT 2880

GGTGGGGGA TTGAGAGGAG ATCATGGGTT TGTGGGAGCA GAGAAGGAAG GTTACACCCA 2940

CAAGTCCAGG GGACATCGAT CATCTGCTGG CCACCATGCC CCCTGTAGTG AGAGTAGCCC 3000

TCTGCTGGCA CTGTCAGAGC GCCCTTCTGC CTGGGACACT CCGATTCCTG TCCCTTCTCT 3060

AAACCCAGGC AGTGGGCAAA CTGGTCTGTC CAGGGTCCTG AGGCAGCTGC AGCCTGGTGG 3120

CTTCGGGGGT GAATCTCAGT GCTTGTGGCA CTATTTCAGG GAATAGGAAA GACACTAAAG 3180

TAAATATTAT TTGCCCCAGC CTCGAACTCA ACACGTCCCA GAGTCCCTCA CCAACCCTGT 3240

CCCGACCCAA CCGGTGCTCT GGGCTCCGTT TCTGGTGTGG GGTCTCACCC CGCACTAGGG 3300

CTGGAAACCT CTGCCCTACC GCCACCCCCT GCCGGGTGCC GCGTGGTGGT AATTTACTGC 3360

TGCAGAGAGC CTCACCTCTC CTCTTTCCCT CCTCTCTATT CCTGCCGCCT GCCCGTGCCC 3420

ACTGAATAAC ATCCCAGCCT CTGACATTGA CAGTCATGTG CGTTAGGATC AGGCTTACCT 3480

GGCTTTCTCG CTTTCTTGCC TCCAGCTCAG CAGCTGCCAC TGCCTGTCCC ACACCTTGAC 3540

TGTCCCATCC CAGGCTACGG GCAAGCTGCT GTCCTCCCCA GAAACCCTTG TCAGTGTGGA 3600

TCTTCTCCCG GAGGAAACAA GAGCGCCTGT CCAGCACACT GTCTCTTTTT TACAGTACTG 3660

AACACTTTTT CACAGTTTGT GAACCCATTC ACCTCTCCAT ATTGAACAGC TTAAGGGCGA 3720

AGTGCTGGCC TAAGGCACTC TAGGACCCAC TGCACCCCGA ACAGACTCGT GGAAATATTT 3780

GTCAATGACC AGAGAAACCA GCACACCCTG GCCCATGGCC ACTCCCACCT GCCCGAGGTT 3840

TTAACCAGTG CCCTTCCTCT CTTTGCAGCC AGACCTCACT CGGCTGTGGG CCTCTCCCCA 3900

GTTCTGCAAA GGCTGTAGTT GTCTGTGATC TTGACTCTCC CCTGCACAGG GAGAAGAATG 3960

ATTCTGACAC TTGGGGACCA GCCTTCAGTA GCTACCCTTG GAATGCCTTT GCTCTCTTCT 4020

CTCCTGTCTA AACAACAAAG AGACGGAGTC TGAGGCCTCA AATTTTCAGT TTGATTTAAG 4080

CATCAAGTTC AAACTTTAGA ACCTGAGCAA ATGTTAGTGA CTCTCCATTG GTTCGTACCT 4140

GGAATGCGCA TCCCCACAGG GGCTTTGTTC TTGGGCCTGG CTGTCTGTGG TCACCAAGTG 4200
```

```
ATGGCCAAAC GGGTGGTGAA AGATGCTGTG TAGGAGGAAT CCACATTGTT AAGAATTC     4258
```

(2) INFORMATION FOR SEQ ID NO:6:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met His Leu Ser Gln Leu Leu Ala Cys Ala Leu Leu Leu Thr Leu
1               5                  10                  15

Leu Ser Leu Arg Pro Ser Glu Ala Lys Pro Gly Ala Pro Pro Lys
            20                  25                  30

Val Pro Arg Thr Pro Pro Ala Glu Glu Leu Ala Glu Pro Gln Ala
            35                  40                  45

Ala Gly Gly Gly Gln Lys Lys Gly Asp Lys Ala Pro Gly Gly Gly
            50                  55                  60

Gly Ala Asn Leu Lys Gly Asp Arg Ser Arg Leu Leu Arg Asp Leu
            65                  70                  75

Arg Val Asp Thr Lys Ser Arg Ala Ala Trp Ala Arg Leu Leu Gln
            80                  85                  90

Glu His Pro Asn Ala Arg Lys Tyr Lys Gly Ala Asn Lys Lys Gly
            95                  100                 105

Leu Ser Lys Gly Cys Phe Gly Leu Lys Leu Asp Arg Ile Gly Ser
            110                 115                 120

Met Ser Gly Leu Gly Cys
            125
```

(2) INFORMATION FOR SEQ ID NO:7:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met His Leu Ser Gln Leu Leu Ala Cys Ala Leu Leu Leu Thr Leu
1               5                  10                  15

Leu Ser Leu Arg Pro Ser Glu Ala Lys Pro Gly Ala Pro Pro Lys
            20                  25                  30

Val Pro Arg Thr Pro Pro Ala Glu Glu Leu Ala Glu Pro Gln Ala
            35                  40                  45

Ala Gly Gly Gly Gln Lys Lys Gly Asp Lys Ala Pro Gly Gly Gly
            50                  55                  60

Gly Ala Asn Leu Lys Gly Asp Arg Ser Arg Leu Leu Arg Asp Leu
            65                  70                  75

Arg Val Asp Thr Lys Ser Arg Ala Ala Trp Ala Arg Leu Leu Gln
            80                  85                  90

Glu His Pro Asn Ala Arg Lys Tyr Lys Gly Ala Asn Lys Lys Gly
            95                  100                 105

Leu Ser Lys Gly Cys Phe Gly Leu Lys Leu Asp Arg Ile Gly Ser
            110                 115                 120
```

```
Met Ser Gly Leu Gly Cys
              125

(2) INFORMATION FOR SEQ ID NO:8:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATGCATCTCT CCCAGCTGCT GGCCTGCGCC CTGCTGCTCA CGCTGCTCTC CCTCCGGCCC    60

TCCGAAGCCA AGCCCGGGGC GCCGCCGAAG GTCCCGCGAA CCCCGCCGGC AGAGGAGCTG   120

GCCGAGCCGC AGGCTGCGGG CGGCGGTCAG AAGAAGGGCG ACAAGGCTCC CGGGGGCGGG   180

GGCGCCAATC TCAAGGGCGA CCGGTCGCGA CTGCTCCGGG ACCTGCGCGT GGACACCAAG   240

TCGCGGGCAG CGTGGGCTCG CCTTCTGCAA GAGCACCCCA ACGCGCGCAA ATACAAAGGA   300

GCCAACAAGA AGGGCTTGTC CAAGGGCTGC TTCGGCCTCA AGCTGGACCG AATCGGCTCC   360

ATGAGCGGCC TGGGATGT                                                 378
```

What is claimed is:

1. An isolated polypeptide having the following amino acid sequence: (SEE SEQ ID NO: 1)

```
Met His Leu Ser Gln Leu Leu Ala Cys Ala

Leu Leu Leu Thr Leu Leu Ser Leu Arg Pro

Ser Glu Ala Lys Pro Gly Ala Pro Pro Lys

Val Pro Arg Thr Pro Pro Ala Glu Glu Leu

Ala Glu Pro Gln Ala Ala Gly Gly Gly Gln

Lys Lys Gly Asp Lys Ala Pro Gly Gly Gly

Gly Ala Asn Leu Lys Gly Asp Arg Ser Arg

Leu Leu Arg Asp Leu Arg Val Asp Thr Lys

Ser Arg Ala Ala Trp Ala Arg Leu Leu Gln

Glu His Pro Asn Ala Arg Lys Tyr Lys Gly

Ala Asn Lys Lys Gly Leu Ser Lys Gly Cys

Phe Gly Leu Lys Leu Asp Arg Ile Gly Ser

Met Ser Gly Leu Gly Cys.
```

2. An isolated polypeptide having the following amino acid sequence: (SEE SEQ ID NO: 2)

```
Asp Leu Arg Val Asp Thr Lys Ser Arg Ala

Ala Trp Ala Arg Leu Leu Gln Glu His Pro

Asn Ala Arg Lys Tyr Lys Gly Ala Asn Lys

Lys Gly Leu Ser Lys Gly Cys Phe Gly Leu

Lys Leu Asp Arg Ile Gly Ser Met Ser Gly

Leu Gly Cys.
```

3. An isolated DNA coding for a polypeptide having the following amino acid sequence (SEE SEQ ID NO: 1)

```
Met His Leu Ser Gln Leu Leu Ala Cys Ala

Leu Leu Leu Thr Leu Leu Ser Leu Arg Pro

Ser Glu Ala Lys Pro Gly Ala Pro Pro Lys

Val Pro Arg Thr Pro Pro Ala Glu Glu Leu

Ala Glu Pro Gln Ala Ala Gly Gly Gly Gln

Lys Lys Gly Asp Lys Ala Pro Gly Gly Gly

Gly Ala Asn Leu Lys Gly Asp Arg Ser Arg

Leu Leu Arg Asp Leu Arg Val Asp Thr Lys

Ser Arg Ala Ala Trp Ala Arg Leu Leu Gln

Glu His Pro Asn Ala Arg Lys Tyr Lys Gly

Ala Asn Lys Lys Gly Leu Ser Lys Gly Cys

Phe Gly Leu Lys Leu Asp Arg Ile Gly Ser

Met Ser Gly Leu Gly Cys.
```

4. An isolated DNA coding for a polypeptide having the following amino acid sequence (SEE SEQ ID NO: 4)

```
Asp Leu Arg Val Asp Thr Lys Ser Arg Ala

Ala Trp Ala Arg Leu Leu Gln Glu His Pro

Asn Ala Arg Lys Tyr Lys Gly Ala Asn Lys
```

-continued

Lys Gly Leu Ser Lys Gly Cys Phe Gly Leu

Lys Leu Asp Arg Ile Gly Ser Met Ser Gly

Leu Gly Cys.

5. A DNA according to claim 3 which has the following base sequence: (SEE SEQ ID NO: 5)

ATG CAT CTC TCC CAG CTG CTG GCC TGC GCC

CTG CTG CTC ACG CTG CTC TCC CTC CGG CCC

TCC GAA GCC AAG CCC GGG GCG CCG CCG AAG

GTC CCG CGA ACC CCG CCG GCA GAG GAG CTG

GCC GAG CCG CAG GCT GCG GGC GGC GGT CAG

AAG AAG GGC GAC AAG GCT CCC GGG GGC GGG

GGC GCC AAT CTC AAG GGC GAC CGG TCG CGA

CTG CTC CGG GAC CTG CGC GTG GAC ACC AAG

TCG CGG GCA GCG TGG GCT CGC CTT CTG CAA

-continued

GAG CAC CCC AAC GCG CGC AAA TAC AAA GGA

GCC AAC AAG AAG GGC TTG TCC AAG GGC TGC

TTC GGC CTC AAG CTG GAC CGA ATC GGC TCC

ATG AGC GGC CTG GGA TGT.

6. A DNA according to claim 4 which has the following base sequence: (SEE SEQ ID NO: 4)

GAC CTG CGC GTG GAC ACC AAG TCG CGG GCA

GCG TGG GCT CGC CTT CTG CAA GAG CAC CCC

AAC GCG CGC AAA TAC AAA GGA GCC AAC AAG

AAG GGC TTG TCC AAG GGC TGC TTC GGC CTC

AAG CTG GAC CGA ATC GGC TCC ATG AGC GGC

CTG GGA TGT.

7. An isolated DNA having the base sequence shown in FIG. 2 (SEQ ID NO: 5).

* * * * *

UNITED STATES PATENT AND TRADEMARK OFFICE
CERTIFICATE OF CORRECTION

PATENT NO. : 6,034,231
DATED : March 7, 2000
INVENTOR(S) : Tanaka et al.

It is certified that error appears in the above-identified patent and that said Letters Patent is hereby corrected as shown below:

On the title page, Please change "Suntory Limited, Osaka, Japan"

to

--Suntory Limited and Hisayuki Matsuo, both of Osaka, Japan--.

Signed and Sealed this

Twenty-second Day of August, 2000

Attest:

Q. TODD DICKINSON

*Attesting Officer*  *Director of Patents and Trademarks*